(12) United States Patent
White et al.

(10) Patent No.: US 11,583,614 B2
(45) Date of Patent: Feb. 21, 2023

(54) HYDROTHERAPY DEVICE

(71) Applicant: John V. White, MD, LLC, Niles, IL (US)

(72) Inventors: John V. White, Lake Forest, IL (US); John D McKenzie, Park Ridge, IL (US)

(73) Assignee: John V. White, MD, LLC, Niles, IL (US)

( * ) Notice: Subject to any disclaimer, the term of this patent is extended or adjusted under 35 U.S.C. 154(b) by 718 days.

(21) Appl. No.: 16/422,929

(22) Filed: May 24, 2019

(65) Prior Publication Data
US 2019/0358374 A1 Nov. 28, 2019

Related U.S. Application Data

(60) Provisional application No. 62/676,143, filed on May 24, 2018.

(51) Int. Cl.
*A61M 1/00* (2006.01)
*A61M 3/02* (2006.01)

(52) U.S. Cl.
CPC .......... *A61M 1/0062* (2013.01); *A61M 3/022* (2014.02); *A61M 2210/086* (2013.01)

(58) Field of Classification Search
CPC ................ A61M 1/0062; A61M 3/022; A61M 2210/086; A61M 35/00; A61M 35/003; A61M 16/0463; A61M 1/92; A61M 1/94; A61M 1/85; A61M 1/006; A61M 1/0058; A61C 17/0208
See application file for complete search history.

(56) References Cited

U.S. PATENT DOCUMENTS

| | | | |
|---|---|---|---|
| 2,238,541 A * | 4/1941 | Vincent | A61H 9/0028 15/257.1 |
| 3,574,239 A | 4/1971 | Sollerud | |
| 4,052,002 A | 10/1977 | Stouffer et al. | |
| 5,735,833 A * | 4/1998 | Olson | A61H 9/0028 604/289 |
| 5,941,859 A * | 8/1999 | Lerman | A61M 3/0287 604/289 |
| 6,406,447 B1 | 6/2002 | Thrash et al. | |
| 6,638,236 B2 | 10/2003 | Thrash et al. | |
| 7,364,565 B2 | 4/2008 | Freeman | |
| 7,578,808 B2 | 8/2009 | Fujisato | |
| 8,362,315 B2 | 1/2013 | Aali | |

(Continued)

FOREIGN PATENT DOCUMENTS

| | | |
|---|---|---|
| FR | 449826 | 3/1913 |
| WO | 2006077292 A1 | 7/2006 |

*Primary Examiner* — Adam Marcetich
*Assistant Examiner* — Rachel O'Connell
(74) *Attorney, Agent, or Firm* — K&L Gates LLP

(57) ABSTRACT

A hydrotherapy device for treating a wound on a surface of a patient's body is provided. A body of the hydrotherapy device includes a wall having an outer surface, an inner surface, and a chamber defined by the inner surface. The wall further includes an internal void, a first port extending fully through the wall and in communication with the void, a second port extending from the outer surface partially through the wall and in communication with the void, and a plurality of channels, each extending from the void to the inner surface. A central axis of each channel forms an angle at the inner surface.

13 Claims, 5 Drawing Sheets

(56) References Cited

U.S. PATENT DOCUMENTS

| | | | |
|---|---|---|---|
| 8,500,661 B2 | 8/2013 | Greenberg | |
| 9,198,801 B2* | 12/2015 | Weston | A61M 1/0001 |
| 9,333,282 B2 | 5/2016 | Van der Hulst | |
| 2003/0204200 A1* | 10/2003 | Rufener | A61M 1/85 |
| | | | 606/172 |
| 2007/0173751 A1* | 7/2007 | Ohashi | A61H 9/005 |
| | | | 601/169 |
| 2013/0085442 A1* | 4/2013 | Shtul | A61B 1/31 |
| | | | 604/28 |
| 2014/0296751 A1 | 10/2014 | Greenberg | |
| 2016/0213823 A1* | 7/2016 | Walborn | A61F 5/0102 |
| 2016/0367398 A1* | 12/2016 | Morgan | A61M 3/022 |

* cited by examiner

HYDROTHERAPY DEVICE

CROSS-REFERENCE TO RELATED APPLICATIONS

This application incorporates by reference and claims the benefit of priority to U.S. Provisional Application 62/676,143 filed on May 24, 2018, the entirety of which is hereby incorporated by reference.

BACKGROUND OF THE INVENTION

The present invention describes a hydrotherapy device for wound treatment. Specifically, the present application describes a hydrotherapy device that creates a vortex motion around a wound within a chamber.

A common problem of wound care is facilitating the washing, cleaning, and sterilizing of a specific wound site which may be difficult to access or is overly sensitive. For hospitals and other healthcare facilities, the problem is particularly amplified because inadequate washing of wounds leading to the increased risk of infection. Washing each wound by hand or through traditional methods is impractical and inefficient, and may be ineffective in clearing the wound debris. In some cases, such as situations in which the wound is in a sensitive location or particularly difficult location, washing may have to be conducted in a bathroom or otherwise non-sterile setting, or require an elaborate setup.

Currently available hydrotherapy devices that facilitate fluid-scavenging for wound irrigation and care have typically included a combination of a suction cup system to evacuate fluid delivered at high pressure through an irrigation tube and/or a nozzle to the wound site. Such pressure is often necessary in single jet systems to dislodge debris and effectively clean the wound site. A few wound irrigation systems include a suction-based delivery system that allows fluid to reach the injury site at a sufficient pressure to remove debris from the wound and recaptures the fluid using a vacuum source.

However, direct fluid sprays (often from direct input lines attached to external fluid sources) are harsh on the wound site and create splash back at the confluence of the wound and the fluid stream. Additionally, such streams are not conducive to easy draining of the fluid, leading to backup of effluent and other contaminated waste including wound debris loosened from the input spray. Such systems may utilize vacuum pumps for sealing and removing wound waste but these systems can be rendered ineffective depending on the type of fluid input system. Finally, current systems of wound care often have spaces either too large or too small between the wound and the source of fluid, necessitating either devices custom-made for the wound or ineffective methods of washing and rinsing wounds through sponges placed onto the wound.

Accordingly, there is a need for an apparatus facilitating a vacuum-powered hydrotherapy device that utilizes a vacuum source to control the fluid delivery and includes angled input channels to create a vortex around the wound within the device.

BRIEF SUMMARY OF THE INVENTION

To meet the needs described above and others, the present disclosure provides a hydrotherapy device that utilizes angled input channels and a vacuum source to create a vortex effect around a wound, which facilitates an even and proper disbursement of fluid around the wound while simultaneously allowing for effective and complete debris removal from the wound site.

By providing a chamber with angled fluid input channels and a vacuum source secured to an opening above the wound, the hydrotherapy device causes fluid to approach the wound in a swirl pattern in order to better clean the wound and dislodge any residual debris from the wound site. The debris and contaminated water are quickly and effectively removed from the chamber by the vacuum source secured to a surface of the hydrotherapy device opposite the wound.

In one embodiment, the hydrotherapy device includes a body with an annular wall integral with a base defining a chamber within. The annular wall has a thickness of about 10 mm, although the thickness as desired or necessitated by manufacturing. During use, the rim of the annular wall is positioned so that the wound is enclosed within the chamber of the device.

Near the rim along an inner surface of the annular wall, the device body includes a plurality of spaced fluid delivery openings through which the fluid enters the chamber. A plurality of channels extends within the thickness of the body between these openings and an input port positioned on an outer surface of the base. Tubing connected to a fluid source is secured to the first port during use of the hydrotherapy device on a user. At each fluid delivery opening, the respective channel meets the inner surface of the annular wall at an angle so that the fluid enters the chamber in a spiral pattern. In one embodiment, the fluid is purified and sterile water, but any suitable fluid for wound care may be utilized in the present invention.

An output port on the back surface extends through the thickness of the body between the outer and inner surfaces of the base. During use, tubing connected to a vacuum source is secured to the output port. With the vacuum source activated, the suction pulls fluid from the fluid source through the input port and into the chamber of the hydrotherapy device. The suction also creates a seal between the rim of the annular wall and the surface of the user's skin around the wound. The use of the vacuum source prevents fluid from escaping underneath the rim of the body and prohibits the sliding of the hydrotherapy device away from the wound site.

As fluid enters the chamber, the spacing and positioning of the fluid delivery openings allows for fluid to approach the wound evenly from all sides. Further, the fluid exits each opening at an angle relative to the inner surface of the annular wall, creating a spiral or vortex motion around the wound. The vacuum continues to pull the fluid away from the wound towards the back surface of the chamber. The contaminated fluid and any debris swept away by the vortex motion around the wound flows through the back surface into the output tubing.

In a further embodiment, a hydrotherapy device includes lateral and medial sections that together form a boot-shaped device. Similar to the above-described embodiment, the boot-shaped hydrotherapy device includes a first port near the toe and a second port near the upper edge of the device. The channels extending from the internal void to the inner surface may form angles with respect to the inner surface of the hydrotherapy device. In this embodiment, the channels form a spiral pattern within the inner surface of the boot.

In one embodiment of the present invention, a hydrotherapy device for treating a wound on a patient's body includes a body including a wall having an outer surface, an inner surface, and a chamber within the inner surface, wherein the wall further includes an internal void, a first port extending fully through the wall and in communication with the void, a second port extending from the outer surface partially through the wall and in communication with the void, and a plurality of channels, each extending from the void to the inner surface. A central axis of each channel forms an acute angle at the inner surface of the wall. In some embodiments, the hydrotherapy device further includes first tubing to a vacuum source and second tubing to a fluid source. The first tubing is connected to the first port and the second tubing is connected to the second port.

In some embodiments, the acute angle is formed along a plane parallel to the surface of the body. The acute angle may be at least about 45 degrees. Each channel may form a further acute angle at the inner surface along a plane perpendicular to the surface of the body, and the further acute angle may be at least about 45 degrees. In other embodiments, the acute angle is formed along a plane perpendicular to the surface of the body. The acute angle is at least about 45 degrees. In still further embodiments, the acute angle may vary among the plurality of channels.

In some embodiments, each channel has a diameter of between about 1 mm and about 3 mm. The wall may include an edge surface, and the plurality of channels may be adjacent to the edge surface. In other embodiments, the plurality of channels may be distributed along the inner surface of the body.

In another embodiment of the present application, the body includes a first section secured to a second section. The first section and the section may comprise lateral and medial sections, respectively, of a body have a boot-like shape.

In another embodiment of the present application, a method for using a hydrotherapy device to treat a wound of a patient comprising the steps of: providing a hydrotherapy device comprising a body including a wall having an outer surface, an inner surface, and a chamber within the inner surface, wherein the wall further includes an internal void, a first port extending fully through the wall and in communication with the void, a second port extending from the outer surface partially through the wall and in communication with the void, and a plurality of channels, each extending from the void to the inner surface; positioning the chamber around the wound; securing a first end of a first tubing to a vacuum source and a second end of the first tubing to the first port; securing a first end of a second tubing to a fluid source and a second end of the second tubing to the second port; and activating the vacuum source to pull fluid from the fluid source through the first port and into the chamber through the plurality of channels.

The method may further included the step of moving the fluid in a vortex motion within the chamber around the wound. In one embodiment, each channel of the plurality of channels includes a central axis that forms an acute angle with the inner surface.

An object of the hydrotherapy device of the present application is to provide wound care that includes a swirling or vortex motion of fluid around the wound within a contained volume.

A further objective of the hydrotherapy device of the present application is to provide for improved removal of debris from the wound.

A further benefit of the invention is that the hydrotherapy device operates using a vacuum source alone, and without the need for pumping at the fluid source.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE INVENTION

Figure 1:
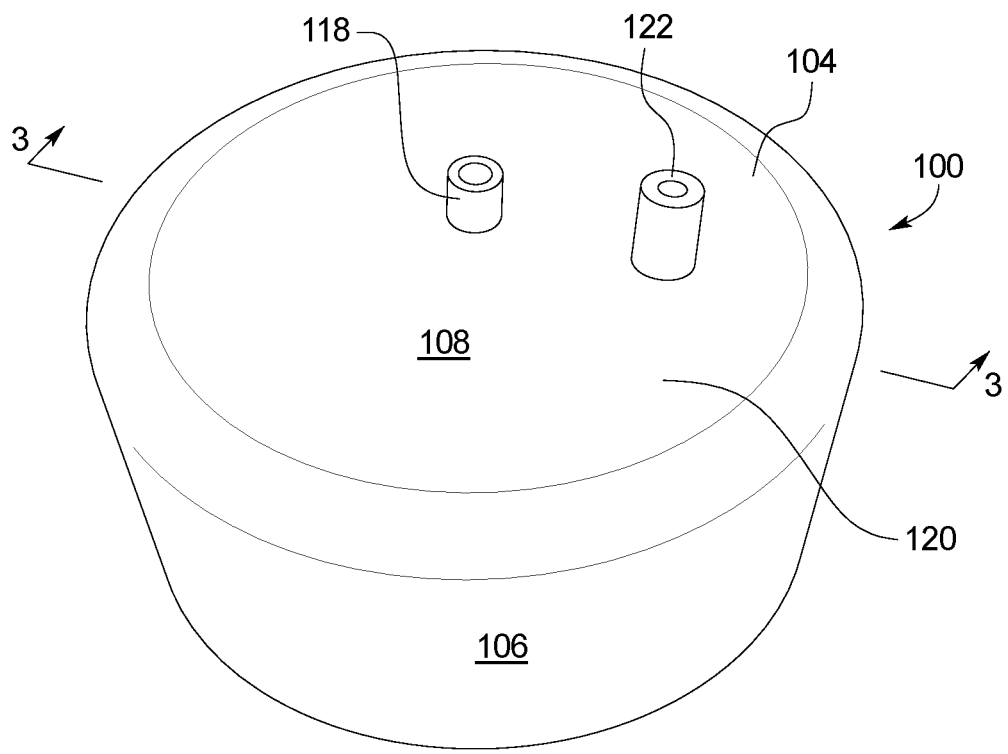
FIG. 1 shows an isometric view from above of a hydrotherapy device of the present application.

In order to meet these needs, the present invention discloses a hydrotherapy apparatus 100 for creating a vacuum-sealed inner chamber containing the wound area and permitting spiral-directional streams of fluid to irrigate the wound with a vacuum source to remove excess debris in a timely and sanitary manner.

FIGS. 1-5 illustrate an example hydrotherapy device 100 including a chamber 102 in which a vortex effect is created for treatment of a wound. The hydrotherapy device 100 includes a body 104 with an annular wall 106 integral with a base 108 defining the chamber 102 within. In other embodiments, the annular wall 106 is semi-spherical and does not include a base. In some embodiments, the annular wall 106 has a thickness T1 of about 10 mm, although the thickness T1 for each of the annular wall 106 may vary as desired or necessitated by manufacturing. Similarly, the thickness of the base 108 may be varied as desired. During use, an edge or rim 110 of the annular wall 106 is positioned so that the wound is enclosed within the chamber 102 of the device 100. While the illustrated embodiment has a cup shape, the hydrotherapy device 100 may have any other shape or size as desired.

Figure 2:
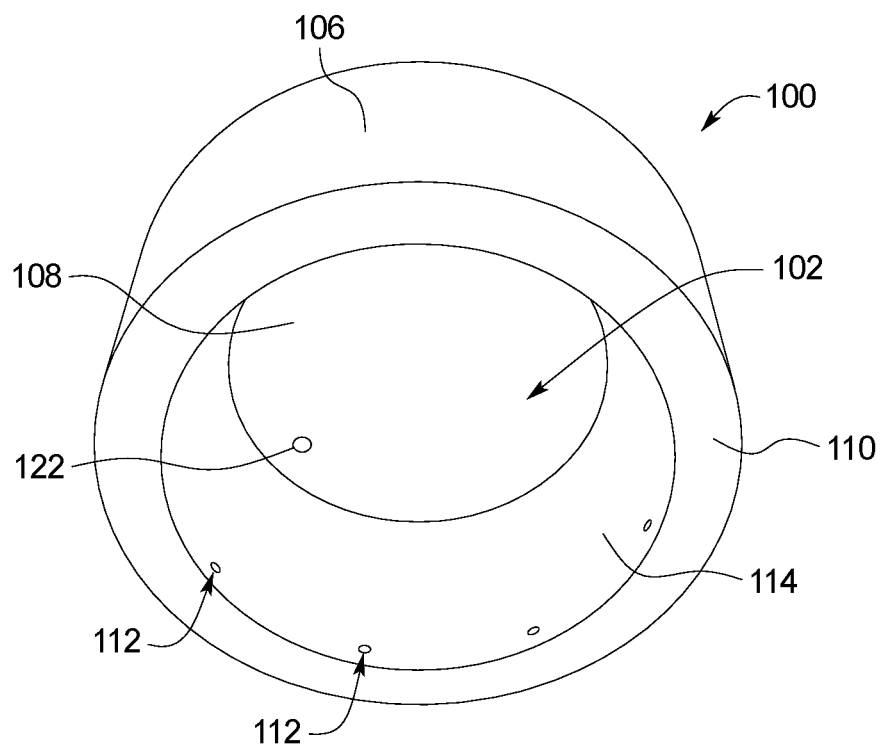
FIG. 2 shows an isometric view from below of the hydrotherapy device of FIG. 1.
Figure 3:
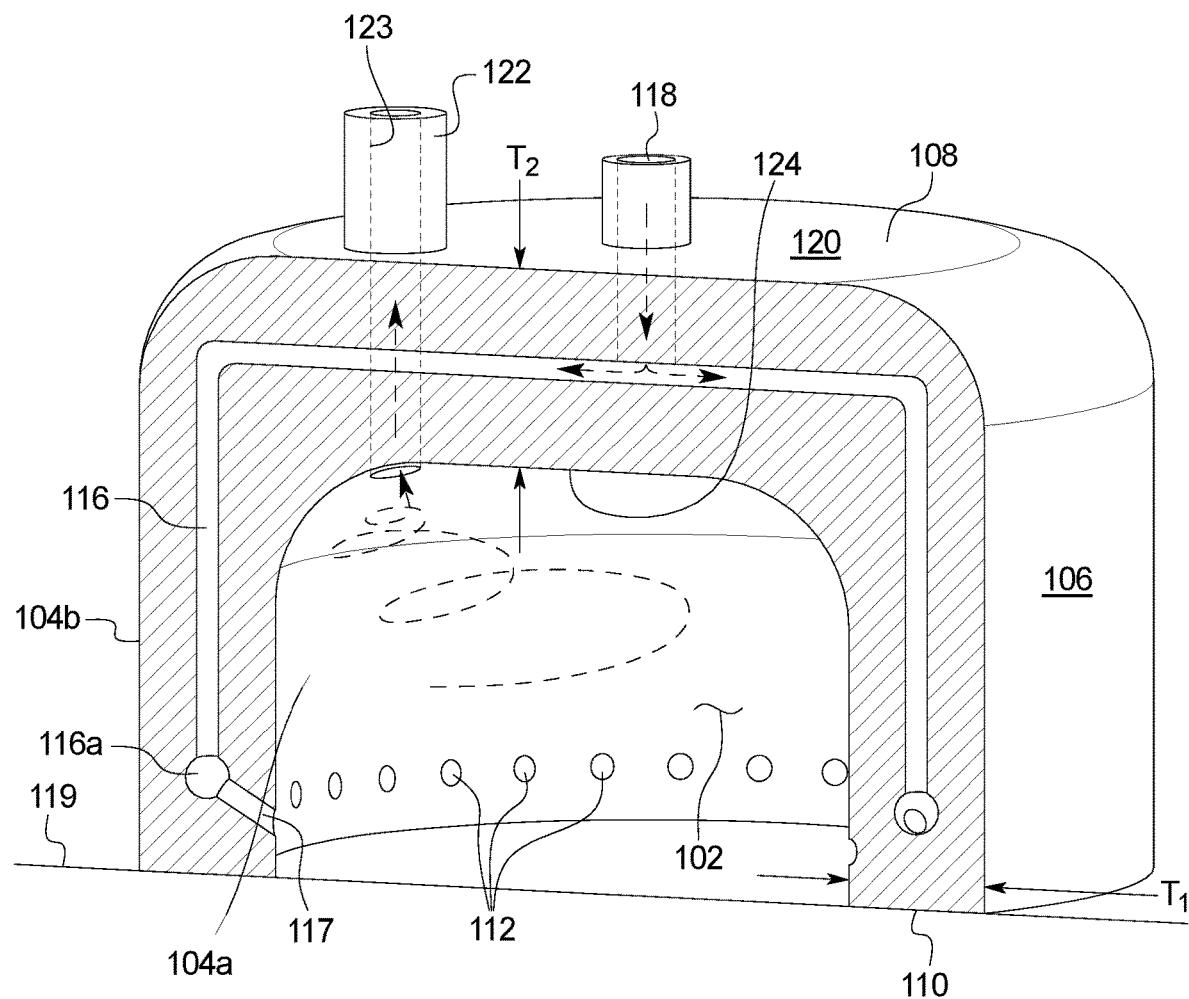
FIG. 3 shows a cross-sectional view of the hydrotherapy device generally taken along lines 3-3 of FIG. 1.
Figure 4:
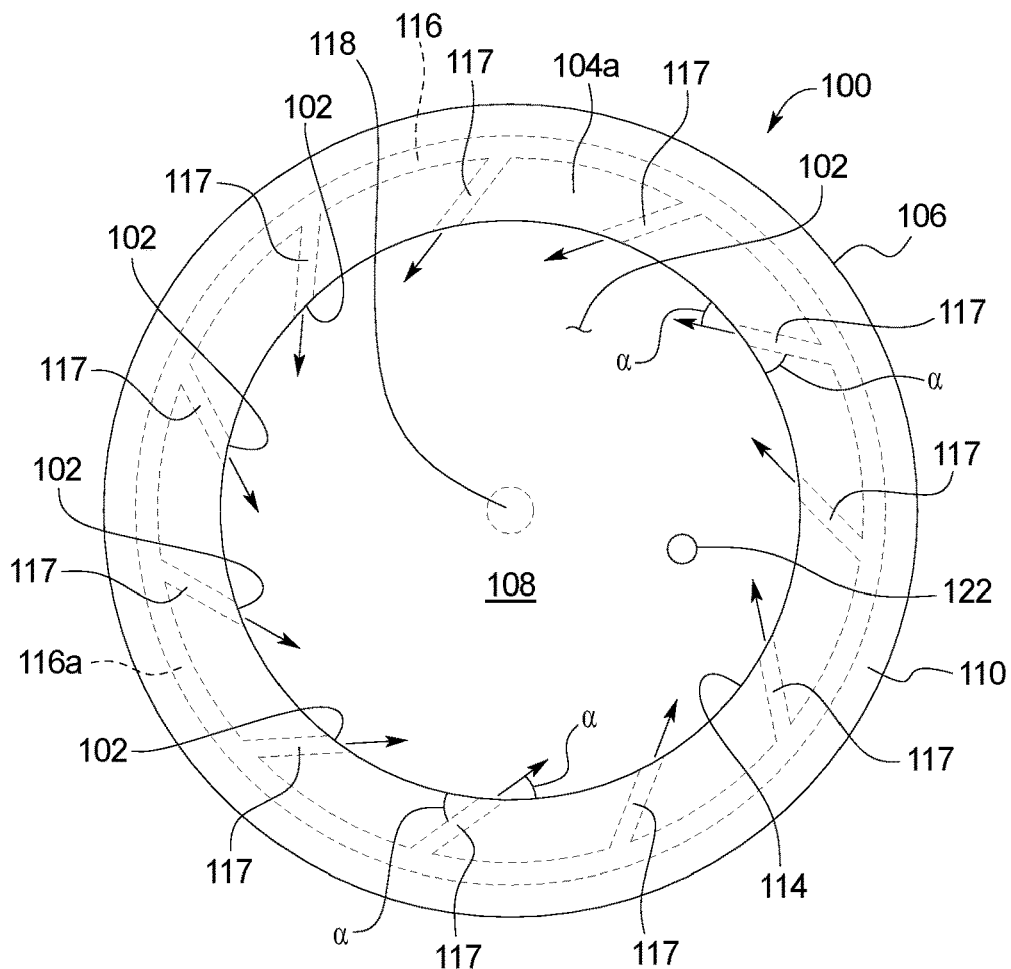
FIG. 4 is a plan view from below of the hydrotherapy device of FIG. 1.
Figure 5:
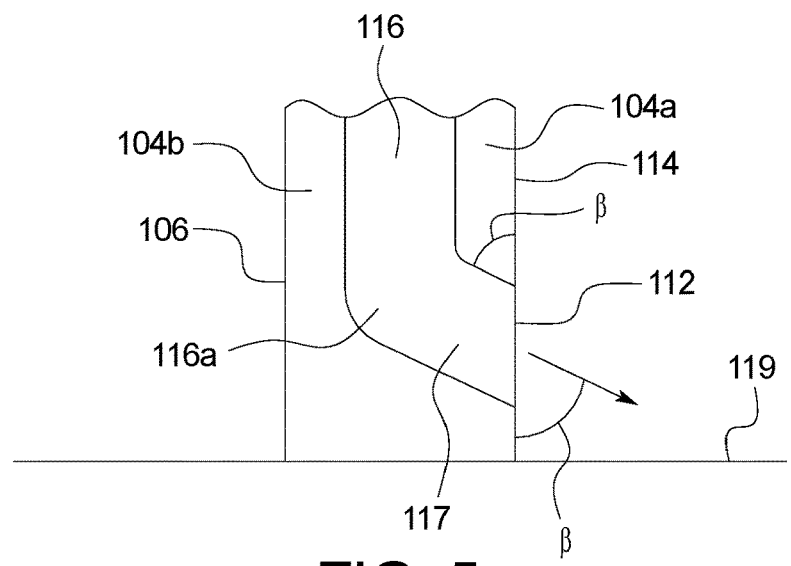
FIG. 5 is an enlarged, cross-sectional view of an opening in the hydrotherapy device of FIG. 1.

Fluid enters the chamber 102 through a plurality of openings 112 spaced along an inner surface 114 of the annular wall 106 adjacent the rim 110 as shown in FIGS. 2 and 3. Referring to FIG. 3, a void 116 is formed along the surface area of the wall 106 within the thickness T1 of the body 104 between an inner portion 104a and an outer portion 104b. The void 116 is in fluid communication with a first port 118 positioned on an outer surface 120 of the base 108. A plurality of channels 117 extends between a terminal channel 116a of the void 116 and the plurality of openings 112. Input tubing (not shown) connected to a fluid source is secured to the input port 118 during use of the hydrotherapy device 100 on a user. During use, fluid enters the hydrotherapy device 100 through the first port 118, travels through the void 116 and the plurality of channels 117 and their respective openings 112, and into the chamber 102.

Similar to the hydrotherapy device 100 of FIGS. 1-5, each of the lateral and medial walls 220, 222 of the lateral and medial sections 202, 204, respectively, includes an enclosed, internal void 218 extending along the surface area thereof. Each section 220, 222 includes a first port 224 extending fully through the wall 220, 222, and a second port 226 extends from the outer surface partially through the wall 220 or 222 and is in fluid communication with the respective void 218. In the illustrated embodiment, the first port 224 is located near the toe 225 of the hydrotherapy device 200 and is connected to a vacuum source via tubing. Similar to the hydrotherapy device 100, an internal tube 227 may be used within the first port 224 to seal off the void 218. The second port 226 is located near the upper end 214 of the hydrotherapy device 200 and is connected to a fluid source via tubing. In other embodiments, the void 218 may be continuous between sections 202, 204.

Referring to FIGS. 1-3, output port 122 in the base 108 extends through the thickness T2 of the body 104 between the outer and inner surfaces 120, 124 of the base 108. During use, second tubing (not shown) connected to a vacuum source is secured to the output port 122. In some embodiments, the second tubing is sized to be positioned within the second port 122 through the base 120 and directly into the chamber, sealing off the void 116. In other embodiments, the hydrotherapy device 100 includes an internal tube 123 within the second port 122 and through the base 120 in order to seal off the void 116. With the vacuum source activated, the suction pulls fluid from the fluid source through the first port 118 and into the chamber 102 of the hydrotherapy device 100. The suction also creates a seal between the rim 110 of the annular wall 106 and the surface of the user's skin around the wound. The use of the vacuum source prevents fluid from escaping underneath the rim 110 of the body 104 and prohibits the sliding of the hydrotherapy device 100 away from the wound site.

The fluid may be a purified and sterile water, although any suitable fluid for wound care may be utilized in the present invention. The hydrotherapy device may also be used for the delivery of pharmaceutical agents, oxygen, and other materials to a wound site. For example, the fluid used for treatment may be a perfluorocarbon material, such as Fluosol-DA, that can deliver oxygen to the tissues and reduce bacterial content through high oxygen partial pressures. Antibiotics and other surface debridement agents, such as nonabsorbable microspheres that are capable of gently debriding tissues, can be added to the fluid prior to connection to the hydrotherapy device. Warming fluids and adding chemotherapeutic agents may provide more direct treatments for skin cancers, such as melanoma.

Figure 6:
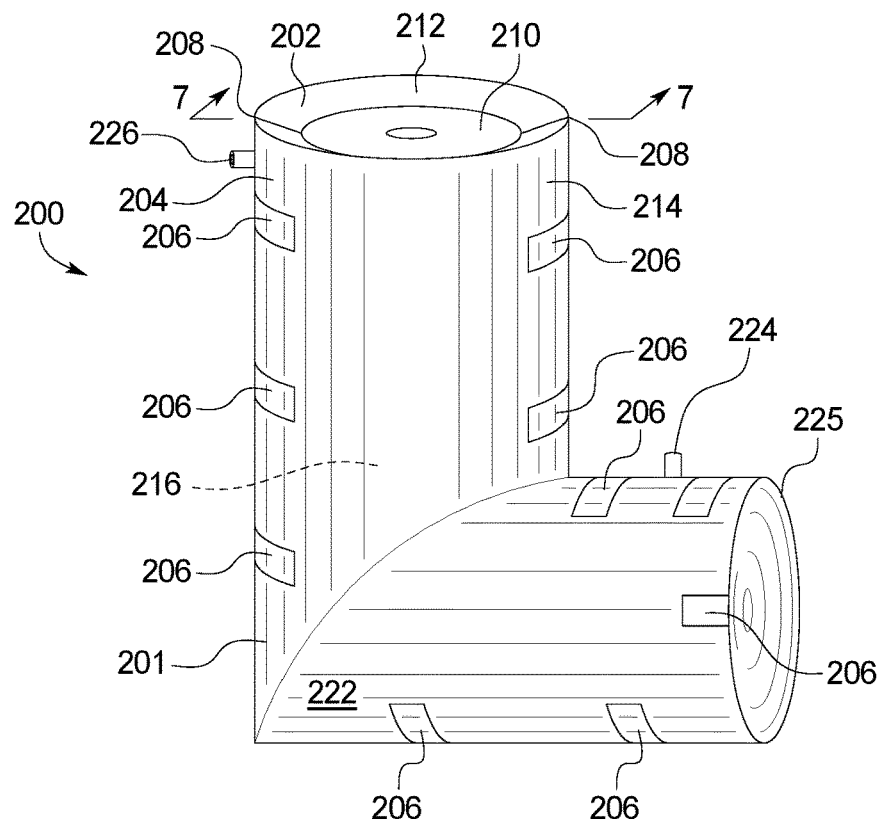
FIG. 6 is a perspective view of a further embodiment of a hydrotherapy device.

FIGS. 6-9 illustrate a further embodiment of a hydrotherapy device 200. The hydrotherapy device 200 has a boot-like shape for providing hydrotherapy to a wound on the calf and/or ankle of the patient. The body 201 includes a lateral section 202 and a medial section 204 joined together using any attachment means 206, such as hook and loop material, to create the boot-like shape. Each of the lateral and medial sections 202, 204 forms a half of the boot-like shape separated along the length of the foot as shown in FIG. 6, although other configurations may be used as desired. A watertight seal such as a neoprene gasket 208 may be applied to the edges of the lateral and medial sections 202, 204 in order to create the watertight seal. The hydrotherapy device 200 further includes a seal 210 along an opening 212 at an upper end 214 of the device 200 to enclose a chamber 216 within the lateral and medial sections 202, 204. The seal 210 may be made of a silicon, neoprene, or other suitable material.

Similar to the hydrotherapy device 100 of FIGS. 1-5, each of the lateral and medial walls 220, 222 of the lateral and medial sections 202, 204, respectively, includes an enclosed, internal void 218 extending along the surface area thereof. Each section 220, 222 includes a first port 224 extending fully through the wall 220, 222, and a second port 226 extends from the outer surface partially through the wall 220 or 222 and is in fluid communication with the respective void 218. In the illustrated embodiment, the first port 224 is located near the toe 226 of the hydrotherapy device 200 and is connected to a vacuum source via tubing. Similar to the hydrotherapy device 100, an internal tube 227 may be used within the first port 224 to seal of the void 218. The second port 226 is located near the upper end 214 of the hydrotherapy device 200 and is connected to a fluid source via tubing. In other embodiments, the void 218 may be continuous between sections 202, 204.

Figure 7:
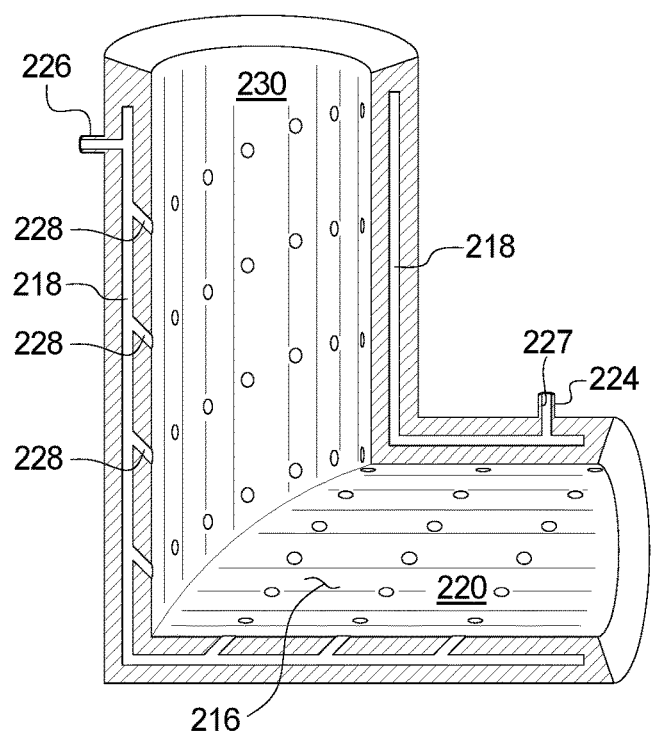
FIG. 7 is a cross-sectional view of the hydrotherapy device of FIG. 6.
Figure 8:
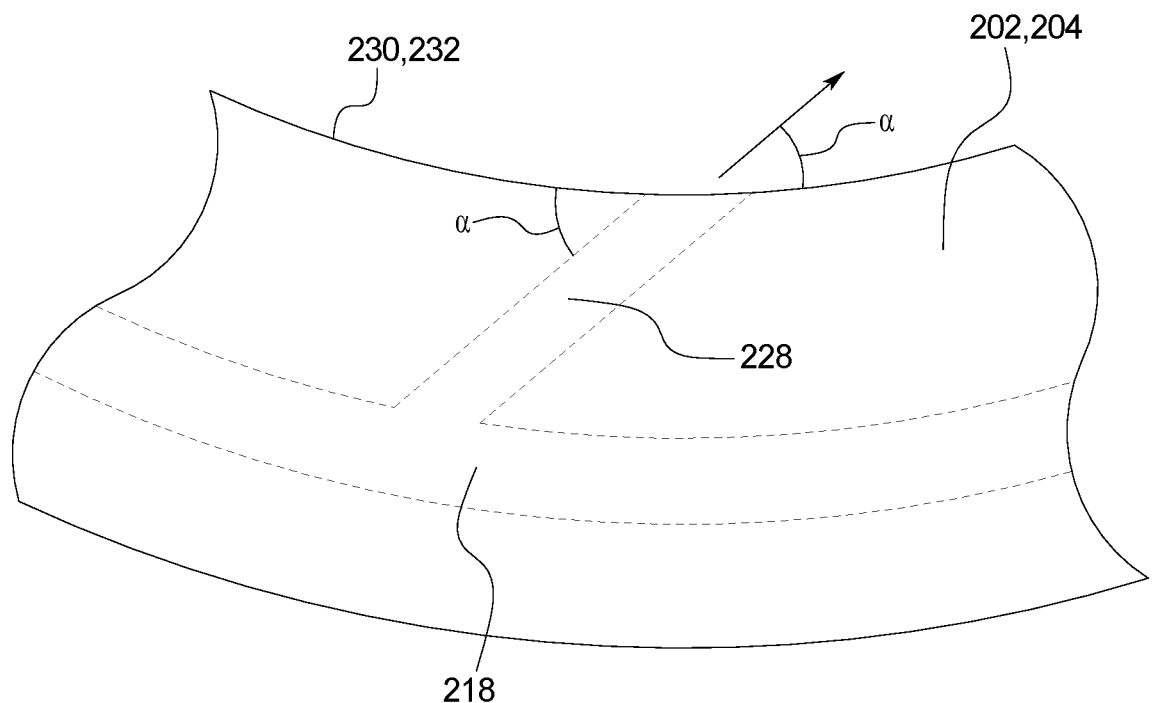
FIG. 8 is a plan view of a channel of the hydrotherapy device of FIG. 6.
Figure 9:
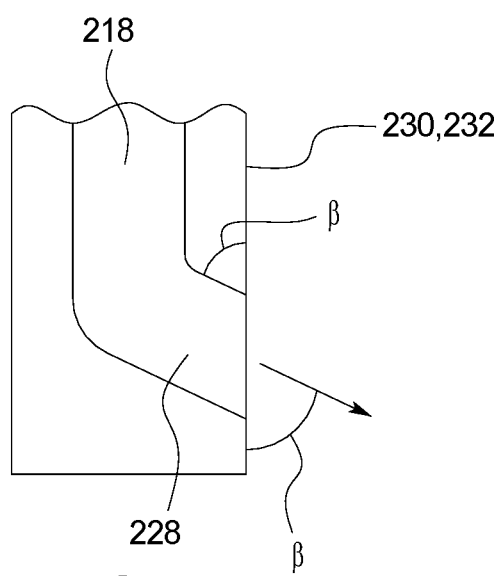
FIG. 9 is a cross-sectional view of the channel of FIG. 8.

Referring to FIGS. 8 and 9, a plurality of channels 228 extend from the void 218 to inner surfaces 230, 232 of the lateral and medial sections 202, 204, respectively, forming an angle α along a central axis of each channel 228 at the inner surface 230, 232 along a plane parallel to the bottom of the patient's foot. Each channel 228 also meets the inner surface 230, 232 at an angle of β along a plane perpendicular to the bottom of the patient's foot. In one embodiment, each of the angles α and β is 45 degrees. The combined angles α and β direct the fluid so that it enters the chamber 216 in a spiral pattern or vortex motion. In some embodiments, the plurality of channels is provided in a spiral pattern, as shown in FIG. 7. In still further embodiments, the channels of the lateral and medial sections 202, 204 are coordinated so that the spiral pattern is a continuous pattern. Further, the angles and size of the channels may vary depending on the target part of the body.

As with the hydrotherapy device 100, tubing is used to connect the first port with a vacuum source and the second port with a fluid source. Activation of the vacuum source pulls fluid from the fluid source, through the second port, into the void, through the plurality of channels, and into the chamber of the device.

In the illustrated embodiment, the shape of the hydrotherapy device 100 approximates a dome or semi-circle, although any shape may used as desired. The dimensions of the hydrotherapy device 100 may be modified as needed. The material is preferably a flexible plastic that conforms to the surface of the body, such as, but not limited to, a silicone material.

It should be noted that various changes and modifications to the presently preferred embodiments described herein will be apparent to those skilled in the art. Such changes and modifications may be made without departing from the spirit and scope of the present invention and without diminishing its attendant advantages.

The invention claimed is:

1. A hydrotherapy device for treating a wound on a surface of a patient's body comprising:
   a body including a wall having an outer surface, an inner surface, a chamber defined by the inner surface, and an edge surface spanning the outer surface and the inner surface, wherein the wall further includes an internal void between the outer surface and the inner surface, an output port extending fully through the inner surface and the outer surface of the wall, an input port in the outer surface of the wall and in communication with the internal void, and a plurality of channels, each channel extending from a terminal channel of the internal void spaced from the edge surface to the inner surface;

wherein a central axis of each channel is angled with respect to the inner surface along first, second, and third planes of a respective coordinate system, wherein the edge surface of the wall is coplanar with the respective first plane and the inner surface is coplanar with the respective second plane at each location where the respective channel meets the inner surface, and wherein each channel extends from the terminal channel through the inner surface toward the respective first plane, and wherein the central axis of each channel is not parallel or perpendicular to any of the respective first, second, and third planes;

wherein the input port is configured for fluid to enter the internal void of the wall through the plurality of channels into the chamber of the body; and wherein the output port is configured for fluid to be pulled out of chamber of the body.

2. The hydrotherapy device of claim 1, further comprising first tubing to a vacuum source and second tubing to a fluid source, wherein first tubing is connected to the output port and the second tubing is connected to the input port.

3. The hydrotherapy device of claim 1, further comprising an internal tubing within the output port to seal off the internal void.

4. The hydrotherapy device of claim 1, wherein the central axis of each channel forms a first angle relative to the respective first plane that is other than 90 degrees, forms a second angle relative to the respective second plane that is other than 90 degrees, and forms a third angle relative to the respective third plane that is other than 90 degrees at each location.

5. The hydrotherapy device of claim 4, wherein one of the second angle and the third angle is at least 45 degrees.

6. The hydrotherapy device of claim 5, wherein the other one of the second angle and the third angle is at least 45 degrees.

7. The hydrotherapy device of claim 4, wherein at least one of the first, second, and third angles vary among the plurality of channels.

8. The hydrotherapy device of claim 1, wherein each channel has a diameter of between 1 mm and 3 mm.

9. The hydrotherapy device of claim 1, wherein the plurality of channels is adjacent to the edge surface.

10. The hydrotherapy device of claim 1, wherein the plurality of channels are distributed along the inner surface of the body.

11. The hydrotherapy device of claim 1, wherein the body includes a first section secured to a second section.

12. The hydrotherapy device of claim 11, wherein the first and second sections are lateral and medial sections, respectively, that form a boot shape.

13. The hydrotherapy device of claim 4, wherein the first angle is at least 45 degrees.

* * * * *